United States Patent [19]

Beckerbauer et al.

[11] Patent Number: 5,312,565
[45] Date of Patent: May 17, 1994

[54] NONLINEAR OPTICAL MATERIALS

[75] Inventors: Richard Beckerbauer, Wilmington, Del.; Dennis S. Donald, Mendenhall; Wilson Tam, Boothwyn, both of Pa.; Frederick C. Zumsteg, Jr., Wilmington, Del.

[73] Assignee: E. I. duPont de Nemours and Company, Wilmington, Del.

[21] Appl. No.: 697,124

[22] Filed: May 8, 1991

Related U.S. Application Data

[63] Continuation-in-part of Ser. No. 577,044, Aug. 28, 1990, abandoned.

[51] Int. Cl.$^5$ .................. C09K 19/52; F21V 9/04; G02B 6/00; C07D 211/56
[52] U.S. Cl. .................. 252/582; 252/587; 359/328; 546/223
[58] Field of Search .................. 252/582, 587, 589; 359/328; 546/192, 223

[56] References Cited

U.S. PATENT DOCUMENTS

| | | | |
|---|---|---|---|
| 3,623,871 | 11/1971 | van Poucke | 96/56.5 |
| 3,963,715 | 6/1976 | Baer et al. | 260/250 BN |
| 4,955,977 | 9/1990 | Doa et al. | 252/582 |
| 4,981,614 | 1/1991 | Miyazaki et al. | 252/587 |
| 5,008,043 | 4/1991 | Robello et al. | 252/582 |
| 5,034,277 | 7/1991 | Laschewsky et al. | 428/411.1 |
| 5,061,404 | 10/1991 | Wu et al. | 252/582 |

FOREIGN PATENT DOCUMENTS

| | | | |
|---|---|---|---|
| 0301411 | 7/1988 | European Pat. Off. | G02F 1/35 |
| 0313475 | 12/1988 | European Pat. Off. | G02F 1/35 |
| 0326133 | 1/1989 | European Pat. Off. | C07C 87/62 |
| 0370922 | 12/1989 | European Pat. Off. | G02F 1/35 |
| 0390655 | 3/1990 | European Pat. Off. | C02R 1/35 |
| 0396172 | 4/1990 | European Pat. Off. | C08F 220/34 |
| 0401128 | 4/1990 | European Pat. Off. | . |
| 1927924 | 1/1970 | Fed. Rep. of Germany | . |
| 4175 | 6/1966 | France | . |
| 1058662 | 2/1967 | United Kingdom | . |

OTHER PUBLICATIONS

Chem. Abst., vol. 81, p. 367, Abstract No. 49395, (1974).
Chem. Abst., vol. 82, p. 472, Abstract No. 154631, (1975).
Chem. Abst., vol. 84, p. 544, Abstract No. 150580, (1976).
Journal of the American Chemical Society, vol. 77, pp. 1913-1914, (Apr. 5, 1955).
Chem. Abst., vol. 74, p. 427, Abstract No. 125079W, (1971).
Chem. Abst., vol. 83, p. 16, Abstract No. 126076, (1975).
Chem. Abst., vol. 80, p. 333, abstract no. 70655, (1974).
Chem. Abst., vol. 88, p. 546, abstract no. 50823, (1978).
Chem. Abst., vol. 83, p. 406, abstract no. 192700, (1975).
Chem. Abst., vol. 78, p. 340, abstract no. 135787, (1973).
Chem. Abst., vol. 81, p. 316, abstract no. 13338 (1974).
Chem. Abst., vol. 87, p. 600, abstract no. 22709 (1977).
Journal of the American Chemical Society, Corrodo, C. et al., vol. 1984, no. 2, pp. 281-285.
Chem. Abst., vol. 54, Abstract No. 9837D, (1960).
Tawney, et al., Journal of Organic Chemistry, vol. 26, pp. 15-21, (Jan. 24 1961).
Chem. Abst., vol. 59, p. 462, Abstract No. 9476F (1963).
Chem. Abst., vol. 75, p. 462, Abstract No. 35463 (1971).
Chem. Abst., vol. 79, p. 376, Abstract No. 137069 (1973).
Chem. Abst., vol. 106, p. 616, Abstract No. 101860 (1987).
Chem. Abst., vol. 79, p. 431, Abstract No. 31758 (1973).
(List continued on next page.)

*Primary Examiner*—Philip Tucker

[57] ABSTRACT

Novel organic glass compositions are disclosed which are poled to achieve nonlinear optical properties. Novel compounds useful for making said poled compositions are also disclosed; as are a method and a device for transforming electromagnetic radiation using a nonlinear optical element formed from said compositions; and certain intermediates for making novel compounds.

3 Claims, No Drawings

OTHER PUBLICATIONS

Chem. Abst., vol. 107, p. 71, Abstract No. 60481 (1987).
Chem. Abst., vol. 81, p. 396, Abstract No. 62699 (1974).
Chem. Abst., vol. 110, p. 652, Abstract No. 94671 (1989).
Chem. Abst., vol. 101, p. 581, Abstract No. 23258 (1984).
Chem. Abst., vol. 109, p. 612, Abstract No. 37773, (1968).
Chem. Abst., vol. 112, p. 623, Abstract No. 207807 (1990).
Chem. Abst., vol. 58, Abstract No. 4555D (1962).
Helvetica Chimica Acta, Buechi J. et al., vol. 45, Baselch, pp. 449-456 (1962).
Japanese Abst., vol. 13, (p. 918, (3711) No. 363, (Aug. 14, 1989).
D. S. Chemia, Non-Linear Properties of Organic Molecules and Chrystals, vol. 1, (1987).
Chemical Abstracts 115:59898v (1991) p. 702.
Patent Abstracts of Japan 14:204 (1990) p-1042.
Patent Abstracts of Japan 13:316 (1989) p-900.
Patent Abstracts of Japan 13:316 (1989) P-900.
Patent Abstracts of Japan 12:71 (1987) P-673.
Patent Abstracts of Japan 14:129 (1990) P-1020.
Patent Abstracts of Japan 12:431 (1988) P-786.
Chemical Abstracts 100:53186e (1984) p. 85.
Chemical Abstracts 98:34543t (1983) p. 647.
Chemical Abstracts 62:12390d (1961) p. 72.
De Cat, A., "Synthetic Applications of Difluorocarbene", Bull. Soc. Chim. Belges, vol. 74 (1965) pp. 270-280.
Hackh's Chemical Dictionary, 4th Edition, pp. 298-299 (1972), McGraw-Hill (Eds).

NONLINEAR OPTICAL MATERIALS

CROSS-REFERENCE TO RELATED APPLICATION

This application is a continuation-in-part of U.S. Pat. application Ser. No. 07/577,044 filed Aug. 28, 1990, now abandoned.

FIELD OF THE INVENTION

This invention relates to nonlinear optical materials and their uses and more particularly to nonlinear organic glass materials and their uses for transforming electromagnetic radiation.

BACKGROUND OF THE INVENTION

Second harmonic generation (SHG) involves the conversion of optical waves having an initial wavelength to optical waves having a wavelength which is one-half of the initial wavelength. Common second harmonic generation is achieved by coupling a beam of input waves into a nonlinear optical material wherein wavelength conversion is achieved. Various types of nonlinear optical materials have been reported as suitable for second harmonic generation. Among these are crystalline solids (see, e.g., U.S. Pat. No. 4,909,964), liquid crystals (see, e.g., G. R. Meredith et al., "Characterization of Liquid Crystalline Polymers for Electro-Optic Applications" A.C.S. Symp. Ser., 1983, 233 (Nonlinear Opt. Prop. Org. Polym. Mater.), 109-33), and polymer glasses (see, e.g., K. D. Singer, et al., "Second Harmonic Generation in Poled Polymer Films", Appl. Phys. Lett. 49(5) 1986).

Generally, a glassy material is prepared for nonlinear optical applications such as second harmonic generation by poling, a process wherein the material is cooled while under an electric field from a temperature above its glass transition temperature (Tg) to a temperature below its Tg. Poling allows polar alignment within the glassy material while under an electric field above its Tg. This alignment is locked in by cooling below Tg. Reheating the material above its Tg in the absence of a field generally results in rapid loss of alignment and a corresponding rapid loss of the bulk nonlinear properties desired for applications such as second harmonic generation. The poling of glassy polymers can be restricted by the polymer backbone and/or spacer groups included within the polymer.

Recently certain nonpolymeric organic glasses have been reported in M. Eich et al., "Second Harmonic Generation in Poled Organic Monomeric Glasses", J. Opt. Soc. Am. B. 6(8) pp 1590-1597, 1989, as suitable for second harmonic generation. Reportedly, compared with the case of polymers with attached or doped nonlinear moieties, one can achieve higher densities of nonlinear active groups and hence possibly higher optical nonlinearities in the nonpolymeric organic glasses, since no polymer backbone and spacer groups are incorporated. However, the compounds used, (s)-2-N-α-(methylbenzylamino)-5-nitropyridine and 2-N-(cyclooctylamino)-5-nitropyridine, have relatively low Tgs (i.e., about 0° C. and −10° C. respectively). Inasmuch as these Tgs are too low for most practical applications, the utility of these materials is considered to be limited.

SUMMARY OF THE INVENTION

This invention provides nonlinear organic glass compositions having glass transition temperatures above about 30° C. Included in this invention are poled compositions consisting essentially of a compound having the formula

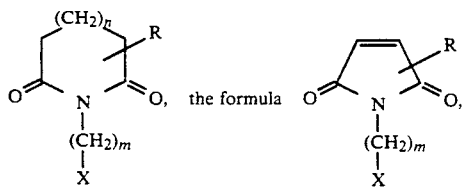

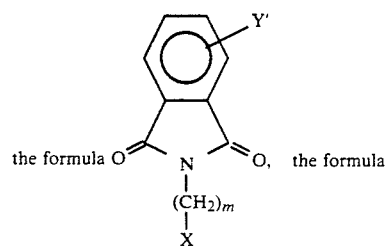

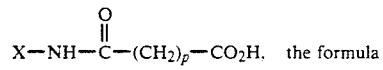

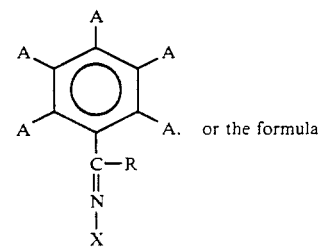

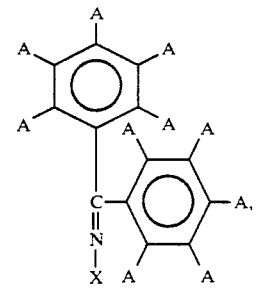

where n is an integer from 0 to 2, m is an integer from 0 to 1, p is an integer from 1 to 20, each A is independently selected from the group consisting of H, OH, $NH_2$, OCOR and $OCH_2CH_2OH$, X is selected from the group consisting of

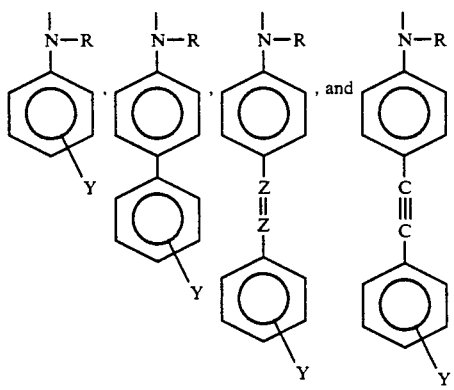

Z is selected from the group consisting of CH and N, Y is selected from the group consisting of H, CN, $NO_2$, $C(CN)=C(CN)_2$, $CO_2R''$, $SO_2 C(A')_3$ and $COC(A')_3$, each A' is independently selected from the group consisting of H, F, Cl, Br, I, alkyl having from 1 to 20 carbon atoms, fluoroalkyl having from 1 to 20 carbon atoms, aryl having from 6 to 12 carbon atoms, SR'' and OR'', R'' is selected from the group consisting of alkyl having from 1 to 20 carbon atoms, R is selected from the group consisting of hydrogen, alkyl groups having from 1 to 20 carbon atoms, and aryl groups having from 6 to 12 carbon atoms, and Y' is selected from the group consisting of R and OR.

Also included in this invention are poled compositions consisting essentially of a compound selected from the group consisting of

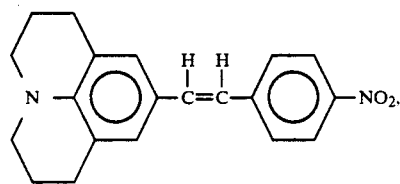

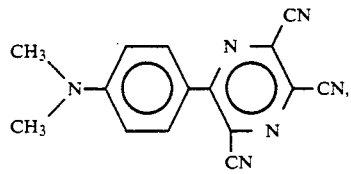

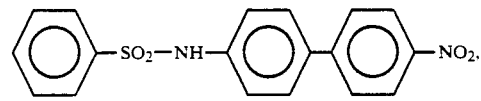

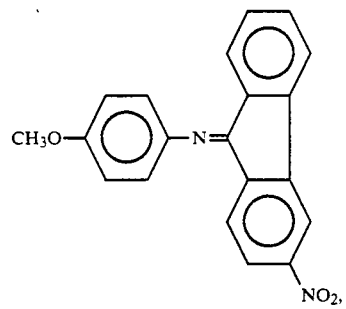

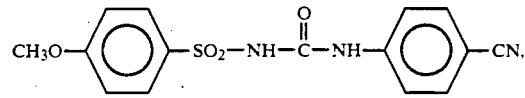

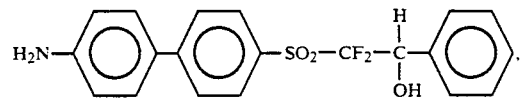

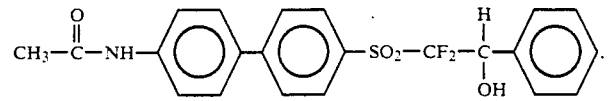

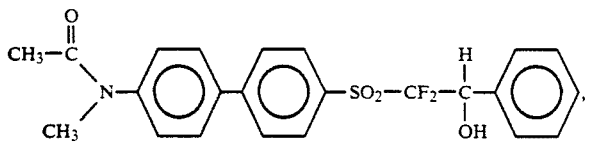

and

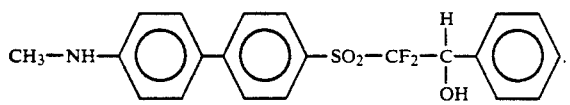

Poled compositions consisting essentially of mixtures of said compounds are also provided in accordance with this invention.

This invention also provides novel compounds useful for making said poled compositions; and a method for transforming electromagnetic radiation using a nonlinear optical element characterized by using such a poled composition as the nonlinear optical element.

DETAILED DESCRIPTION OF THE INVENTION

Nonlinear organic glass compositions are provided by this invention which are formulated from materials which form glasses and which can be poled to develop nonlinear optical properties (e.g., SHG) with advantageous temporal stability. Preferred materials of this type are considered to have a glass transition temperature (i.e., Tg) above about 30° C., and significant hyper-polarizability (e.g., $\beta$, the hyperpolarizability measured by electric field induced second harmonic, EFISH, above about $5 \times 10^{-30}$ D esu, and $\mu\beta$ above about $25 \times 10^{-48}$ esu where $\mu$ is the dipole moment).

The materials have glassy states of sufficient stability to prevent undue crystallization under poling or use conditions. While the organic compositions of this invention are substantially in the form of a glass, a minor amount of crystallinity can be tolerated without loss of the desirable nonlinear optical properties. In general, the presence of significant crystallinity in the glass composition can cause a reduction in functionality. For example, crystallinity can cause increased scattering of the incident radiation, which can significantly decrease the efficiency of any optical device utilizing these glass compositions. Furthermore, depending on the amount, location and type of crystallinity in the glass composition, SHG can be greatly diminished.

The organic glass compositions of this invention include poled compositions consisting essentially of a compound having the formula

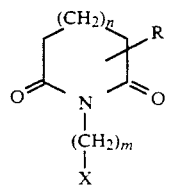

where n is an integer from 0 to 2, m is an integer from 0 to 1, X is selected from the group consisting of

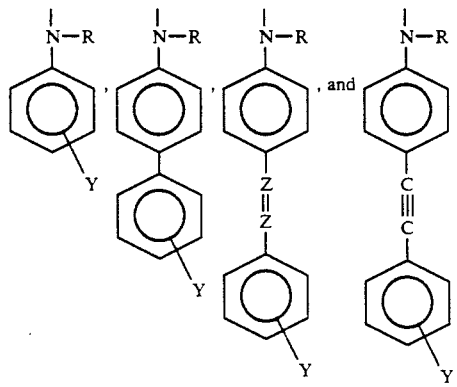

Z is selected from the group consisting of CH and N, Y is selected from the group consisting of H, CN, NO$_2$, C(CN)=C(CN)$_2$, CO$_2$R″, SO$_2$C(A′)$_3$ and COC(A′)$_3$, each A′ is independently selected from the group consisting of H, F, Cl, Br, I, alkyl having from 1 to 20 carbon atoms, fluoroalkyl having from 1 to 20 carbon atoms, aryl having from 6 to 12 carbon atoms, SR″ and OR″, R″ is selected from the group consisting of alkyl having from 1 to 20 carbon atoms, and R is selected from the group consisting of hydrogen, alkyl groups having from 1 to 20 carbon atoms, and aryl groups having from 6 to 12 carbon atoms.

Compounds of this formula where m is 0 may be readily prepared by the reaction of cyclic anhydrides and hydrazines as in Indian Journal of Chem. 23 B pages 439–440 (1984); and compounds of this formula where m is 1 may be readily prepared by the reaction of cyclic imides, formaldehyde and amines as in S. B. Kadin, Monomethylation of Aromatic Amines via Sodium Borohydride Mediated Carbon-Nitrogen Bond Cleavage, J. Org. Chem. 38 (7) 1348–1350 (1973). For example p-nitrophenylhydrazine and glutaric anhydride may be reacted to form N-p-nitroanilinoglutarimide; and methyl-4-aminobenzoate, formaldehyde and succinimide may be reacted to form N-(p-carboxymethylphenyl)aminomethyl succinimide.

Preferably n is either 0 or 1. A preferred R is hydrogen; a preferred X is NHC$_6$H$_4$CH=CHC$_6$H$_4$Y; and preferred Y groups include NO$_2$ and SO$_2$CF$_2$A′ where the A′ is fluoroalkyl. Preferred compounds of this formula include compounds where n is 1; R is hydrogen, m is 0, X is NRC$_6$H$_4$Y and Y is para NO$_2$, para SO$_2$(CF$_2$)$_2$CF$_3$, or para SO$_2$(CF$_2$)$_7$CF$_3$, the compound where n is 1, R is hydrogen, m is 0, X is NRC$_6$H$_4$CH=CHC$_6$H$_4$Y and Y is 4′NO$_2$ (i.e., 4-(p-nitrophenylvinylene)anilinoglutarimide), the compound where n is 1; R is hydrogen, m is 1, X is NRC$_6$H$_4$Y, and Y is para CN or para CO$_2$CH$_3$, and the compound where n is 0, R is H, m is 1, X is NRC$_6$H$_4$CH=CHC$_6$H$_4$, and Y is 4"NO$_2$.

The novel compounds of this invention include compounds of this formula with the proviso that when n is 0, m is 1, each R is H, and X is NRC$_6$H$_4$Y, then Y is not para CN. Examples of novel compounds of this invention include N-p-nitroanilinoglutarimide, N-(p-heptafluoropropylsulfonylphenylamino)glutarimide, N-(p-heptadecylfluorooctylsulfonylphenylamino)-glutarimide, N-4-(p-nitrophenylvinylene)phenylamino-glutarimide, N-4'-nitrobiphenylaminoglutarimide, N-(p-carboxymethylphenyl)aminomethylsuccinimide, and N-4-(p-nitrophenylvinylene)phenylaminomethylsuccinimide.

The organic glass compositions of this invention include poled compositions consisting essentially of a compound having the formula

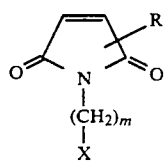

where m, X and R are as defined above. Compounds of this formula may be readily prepared by the reaction of cyclic anhydrides and hydrazines as in Indian Journal of Chem. 23 B pages 439-440 (1984); and compounds of this formula where m is 1 may be readily prepared by the reaction of cyclic imides, formaldehyde and amines as in S. B. Kadin (supra) J. Org. Chem. 38 1348 (1973). For example p-nitrophenylhydrazine may be reacted with maleic acid to form N-p-nitroanilinomaleimide; and aniline may be reacted with formaldehyde and maleimide to form N-phenylaminomethymaleimide. A preferred R is hydrogen; a preferred X is NHC$_6$H$_4$CH=CHC$_6$H$_4$Y; and preferred Y groups include NO$_2$ and SO$_2$CF$_2$A' where the A' is fluoralkyl.

The novel compounds of this invention include compounds of this formula with the proviso that when R is p-chlorophenyl, and m is 0, then X is not 2,4-dinitrophenylamino. Examples of the novel compounds of this invention include N-p-nitroanilinomaleimide, N-(p-heptadecylfluorooctylsulfonylphenylamino)maleimide, N-4-(p-nitrophenylvinylene)phenylaminomaleimide, N-4'-nitrobiphenylaminomaleimide, N-(p-nitrophenyl)-aminomethylmaleimide, and N-4-(p-nitrophenylvinylene)-phenylaminomaleimide.

The organic glass compositions of this invention include poled compositions consisting essentially of a compound having the formula

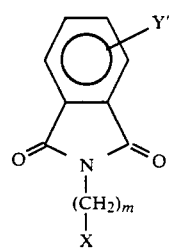

where m and X are as defined above and Y' is selected from the group consisting of R and OR where R is as defined above. Compounds of this formula where m is 0 may be readily prepared by the reaction of cyclic anhydrides and hydrazines as in Indian Journal of Chem. 23 B pages 439-440 (1984); and compounds of this formula where m is 1 may be readily prepared by the reaction of cyclic imides, formaldehyde and amines as in S. B. Kadin (supra) J. Org. Chem. 38 1348 (1973). For example phenylhydrazine may be reacted with phthalimide to form anilinophthalimide; and analine may be reacted with formaldehyde and phthalimide to form N-phenylamino-methylphthalimide. A preferred R is hydrogen, a preferred X is NHC$_6$H$_4$CH=CHC$_6$H$_4$Y, and preferred Y groups include NO$_2$ and SO$_2$CF$_2$A' where the A' is fluoralkyl.

The novel compounds of this invention include compounds of this formula with the proviso that when Y' is H, and m is 0, then X is not 2,4-dinitrophenylamino, and when Y' is H, and m is 1, then X is not phenylamino. Examples of the novel compounds of this invention include N-p-nitroanilinophthalimide, N-(p-heptafluoropropylsulfonylphenylamino)phthalimide, N-4-(p-nitrophenylvinylene)phenylaminomaleimide, N-4'-nitrobiphenylaminophthalimide, and N-(p-nitrophenyl)-aminomethylphthalimide.

The organic glass compositions of this invention include poled compositions consisting essentially of a compound having the formula

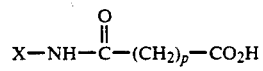

where X is as defined above and p is an integer from 1 to 20. Compounds of this formula may be readily prepared as in Indian Journal of Chem. 23 B pages 439-440 (1984) by the reaction of hydrazines and cyclic anhydrides. For example p-nitrophenylhydrazine and anhydride may be reacted to form N-p-nitro-anilinoglutamic acid (i.e., p is 3, and X is p-nitrophenyl-amino).

The novel compounds of this invention include compounds of this formula with the proviso that when p is 1, then X is not diphenylamino; when p is 2, then X is neither p-nitrophenylamino nor 2,4-dinitrophenylamino; and when p is 2 or 3, then X is not phenylamino. Examples of the novel compounds of this invention include N-p-nitroanilinoglutamic acid, N-p-heptafluoropropylsulfonylphenylaminoglutamic acid, N-4-(p-nitrophenylvinylene)phenylaminoglutamic acid, N-4'-biphenylaminoglutamic acid, and N-p-heptafluoropropylsulfonylphenylaminosuccinamic acid.

The novel glass compositions of this invention include poled compositions consisting essentially of a compound having the formula

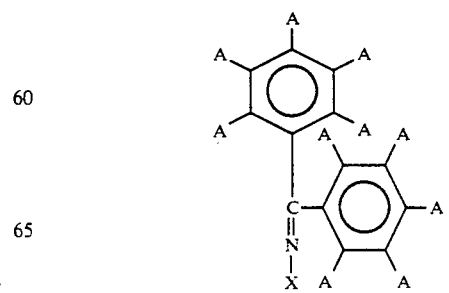

where each A is independently selected from the group consisting of H, OH, NH₂, OCOR and OCH₂CH₂OH, and X and R are as defined above.

A preferred X is NHC₆H₄CH=CHC₆H₄Y; and preferred Y groups include NO₂ and SO₂CF₂A' where the A' is fluoralkyl. Preferred compounds of this formula include those having the formula XNC(C₆H₄A)₂ where the A on each ring is OH or NH₂.

Compounds of this formula may be readily prepared using standard methods for the preparation of hydrazones from ketones and hydraxine, see, E.g. R.L. Shriner et al., "The systematic Identification of Organic Compounds" John Wiley, Inc. NY 4th ed., (1956) page 131. For example p-notrophenylhydrazine may be reacted with dihydroxybenzylphenone.

The novel compounds of this invention include compounds of this formula with the proviso that at least one A is not H. Examples of novel compounds of this invention include p-nitrophenylhydrazone of 4,4'-dihydroxybenzophenone, p-nitrophenylhydrazone or 2,4-dihydroxybenzophenone, p-heptafluoropropysulfonylphenylhydrazone of 4,4'-dihydroxybenzophenone, and p-heptafluoropropylsulfonylphenylhydrazone of 2,4-dihydroxybenzophenone.

The organic glass compositions of this invention include poled compositions consisting essentially of a compound having a formula

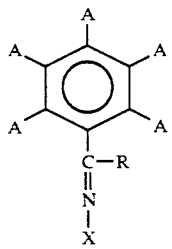

where A, X and R are as defined above. Preferably at least two A groups are selected from OH and NH₂, with any remaining A groups being hydrogen. A preferred R is hydrogen, a preferred X is NHC₆H₄CH=CHC₆H₄Y, and preferred Y groups include NO₂ and SO₂CF₂A' where A' is fluoralkyl. Preferred compounds of this formula include compounds where each A at the meta position of OH and each other A is H, R is H, X is NHC₆H₄Y and Y is para NO₂.

Compounds of this formula may be readily prepared using standard methods for preparation of hydrazones from hydrazines and either ketones or aldehydes, see R. L. Shriner et al. (supra.) For example p-nitrophenylhydrazine may be reacted with 3,5-dihydroxyacetophenone.

The novel compounds of this invention include compounds of this formula with the proviso that when A is H at the 2, 4 and 6 positions and is OH at the 3 and positions, and R is n-butyl, ethyl, methyl, n-hexyl, —CH₂CH₂CH(CH₃)₂ or —CH₂CH(CH₃)₂, then X is not 2,4-dinitrophenylamino; when A is H at the 2, 4 and 6 positions, and is OH at the 3 and 5 positions, and R is methyl, then X is not p-nitrophenylamino; when A is H at the 2 and 6 positions and is OH at the 3, 4 and 5 positions, and R is H or methyl, then X is not p-nitrophenylamino; when A is H at the 2, 3, 5 and 6 positions and is OH at the 4 position, and R is methyl or ethyl, then X is not 2,4-dinitrophenylamino; when A is either H at the 3, 5 and 6 positions and OH at the 2 and 4 positions or H at the 2, 5 and 6 positions and OH at the 3 and 4 positions, and R is H, then X is not 2,4-dinitrophenylamino; when A is either H at 3, 4, 5 and 6 positions and OH at the 2 position, or H at the 2, 4, 5 and 6 positions and OH at the 3 position, or H at the 2, 3, 5 and 6 positions and OH at the 4 position, and R is H, then X is neither p-nitrophenylamino nor 2,4-dinitrophenylamino; when A is H at the 3, 4, 5 and 6 positions and NH2 at the 2 position, and R is H, then X is not p-nitrophenylamino; and when A is H at the 5 and 6 position, OH at the 3 position, Cl at the 2 position and either H or Cl at the 4 position, and R is H, then X is not p-nitrophenylamino. Examples of novel compounds of this invention include p-heptafluoropropylsulfonylphenylhydrazone of 3,5-dihydroxyacetophenone, and p-heptadecylfluorooctylsulfonylphenylhydrazone of 3,4-dihydroxyacetophenone.

As discussed above, certain compounds used for the organic glass compositions (where m is 1) can be prepared by reacting amines, formaldehyde and cyclic imides. This is illustrated in Examples V, VI and VII below. Other compounds used for the organic glass compositions (other than where m is 1) as discussed above can generally be prepared by reacting hydrazines with cyclic anhydrides, aldehydes and ketones. This is illustrated in Examples I, II, III, IV, X, XII and XIII below. Certain hydrazines which can be used as intermediates for the synthesis of embodiments of this latter group of compounds are themselves considered novel. Novel intermediates provided in accordance with this invention include those having the formula R$_f$SO₂C₆H₄NHNH₂, where R$_f$ is a branched Or straight chain perfluoroalkyl group having from 1 to 20 carbon atoms. These novel hydrazine intermediates are particularly useful for preparing compounds where X is NRC₆H₄Y, R is H, Y is SO₂C(A' )₃ and each A' is selected from F and perfluoroalkyl; and are prepared by reacting a p-perfluoroalkylsulfonylfluorobenzene with hydrazine sulfate in a polar solvent at temperatures between 60° C. and 120° C. Specific novel intermediates are heptafluoropropylsulfonylphenylhydrazine, shown in Examples II and XII, and heptadecylfluorooctylsulfonylphenylhydrazine, shown in Examples III and XIII.

The organic glass compositions of this invention include poled compositions consisting essentially of the compound

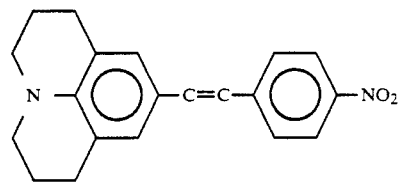

This compound may be prepared using the general method for preparing stilbenes disclosed in U.S. Pat. No. 2,878,291. This is a novel and preferred compound for forming poled compositions of this invention.

The organic glass compositions of this invention include poled compositions consisting essentially of the compound

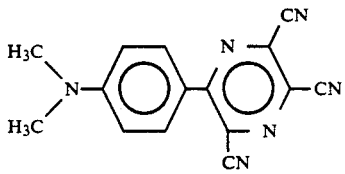

This compound may be prepared as disclosed in U.S. Pat. No. 3,963,715. This is a preferred compound for forming poled compositions of this invention.

The organic glass compositions of this invention include poled compositions consisting essentially of the compound

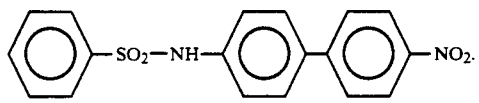

This compound may be prepared by the reaction of 4-nitro-4'-aminobiphenyl with benzene sulfonyl chloride. See Morgan et al., J. Chem. Soc. 91 p. 1507 (1907).

The organic glass compositions of this invention include poled compositions consisting essentially of the compound

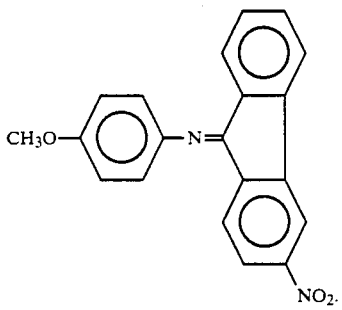

This compound may be prepared by the reaction of p-anisidine with 3-nitro-9-fluorenone.

The organic glass compositions of this invention include poled compositions consisting essentially of the compound

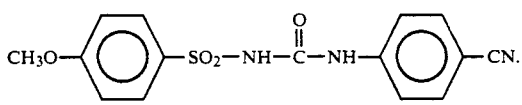

This compound may be prepared by the reaction of p-cyanoaniline with p-methoxyphenylsulfonylisocyanate.

The organic glass compositions of this invention include poled compositions consisting essentially of the compound

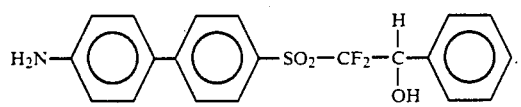

This compound may be prepared using p-trimethyl-triphenyl-$SO_2CF_2C(Ph)(OH)(H)$ and p-$(CH_3C(O))_2$N-phenyl-Br in accordance with Example XI herein.

The organic glass compositions of this invention include poled compositions consisting essentially of the compound

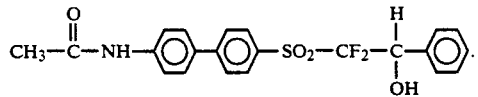

This compound may be prepared by reacting $(CH_3C(O))_2$N-biphenyl-$SO_2CF_2C(Ph)(OH)(H)$ with HCl at room temperature.

The organic glass compositions of this invention include poled compositions consisting essentially of the compound

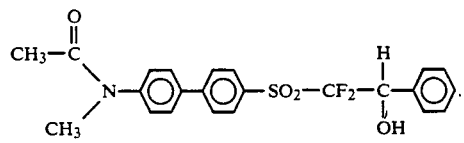

This compound may be prepared by reacting p-$(CH_3)(CH_3C(O))$N-phenyl-Br with p-trimethyltinphenyl-$SO_2CF_2C(Ph)(OH)(H)$.

The organic glass compositions of this invention include poled compositions consisting essentially of the compound

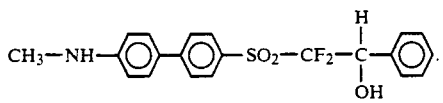

This compound may be prepared by reacting $(CH_3)(CH_3C(O))$N-biphenyl-$SO_2$ $CF_2C(Ph)(OH)(H)$ with HCl.

Mixtures of these compounds may be used to produce the poled organic glass compositions of this invention.

The organic glass compositions of this invention are formed by applying an electric field to a composition consisting essentially of the desired compound(s) when it is in a low viscosity state (i.e., above its Tg) where the molecular dipoles can align in response to the electric field, and then while maintaining the electric field, increasing the viscosity (e.g., by cooling the composition below its Tg) to a point where the molecules have little rotational freedom.

The electric field may be provided using conventional methods.

An electric field for poling is commonly created in one of two ways: corona poling or electrode poling. See, e.g., K. D. Singer et al., "Electro-optic phase modulation and optical second harmonic generation in corona-poled polymer films", Appl. Phys. Lett. 53(19) pp 1800–1802 (1988). In electrode poling the electric field is created between two closely spaced electrodes. Depending on the desired sample configuration, these electrodes can either be in the plane of a thin film, in which case the field is primarily parallel to the surface of the sample; or it can be in a plane above and below the sample, in which case the field is perpendicular to the sample surface. The latter configuration has the advantage of generating high fields over a large area, but has the disadvantage for frequency doubling of requiring that the electrodes are transparent and that the sample is tilted with respect to the input beam. This latter requirement is necessary so that a component of the fundamental beam's electric field can be parallel to the poling direction.

Electric field poling has several disadvantages, particularly when surveying a large number of new materials where the thin film quality and characteristics have not been optimized. Because of the high fields involved, electrochemistry can take place at the electrodes, thereby altering material properties. Also microscopic defects can lead to electrical breakdown at potentials many times smaller than a defect-free film could sustain. Such a breakdown will typically ruin a sample since the entire charge contained on the elctrodes will flow through a small area of the sample causing thermal damage not only to the sample but also to the electrodes.

One method of avoiding these problems is to use corona poling. In this technique, a corona discharge is used to create the electric field by depositing charge on a thin film sample which has been coated on a conductive substrate. This technique eliminates the high voltage electrode and, since there is no conductive electrode to carry charge to a defect, also eliminates the catastrophic damage associated with having a conductive point defect. This technique does, however, have the limitations of requiring a transparent electrode and a tilted sample. In addition, since a corona discharge is a current limited source, modest sample conductivity will cause a reduction in the maximum field which can be generated.

Without limiting the invention to a particular theory of operation. in some embodiments of this invention, the compositions are formulated from molecules which include one component considered to have the dominant role of stabilizing the glass and providing increased viscosity above Tg, and another component considered to have the dominant role of providing the major contribution to the optical nonlinearity. Indeed in some instances compounds of each type can be independently assessed from measurements of glass forming properties of stabilizing groups and measurements of hyperpolarizability of nonlinear optically active groups; and then the compounds can be combined to form molecules useful for forming poled compositions. In some embodiments, however, the functions are considered to be merged within a single molecule such that the contributions of portions of the molecule cannot be clearly delineated.

Organic glass compositions which are poled films are considered particularly useful because of their high concentration of nonlinear optically active molecules, their capability of being formed into large area thin films, and their high orientational stability. Preferred film thickness can vary according to use. Typically film thickness is within the range of 0.5 $\mu$m to 100 $\mu$m.

Poled compositions can be provided in other forms as well (e.g., a solid block of glass could be formed into an electrooptic modulator or a frequency converter using conventional techniques known in the art for single crystals) and organic glass compositions in other forms are also included within this invention.

The poled organic glass compositions of this invention are preferably shaped to function as nonlinear optical elements for transforming electromagnetic radiation (e.g.. by changing the frequency and/or polarization of the radiation); and a method for transforming electromagnetic radiation using a nonlinear optical element is provided in accordance with this invention which is characterized by using a poled organic glass composition provided herein as the nonlinear optical element. Generally, the nonlinear optical element of poled organic glass is used for transforming electromagnetic radiation by including it within an optical device; and a device for transforming electromagnetic radiation using a nonlinear optical element is provided in accordance with this invention which is characterized by using a poled organic glass composition provided herein as the nonlinear optical element. Poled organic glass compositions having glass transition temperatures above 30° C. are particularly advantageous.

As disclosed in U.S. Pat. No. 4,909,964, one conventional type of nonlinear optical device comprises means to direct at least one incident beam of electromagnetic radiation into an optical element having nonlinear optical properties whereby electromagnetic radiation emerging from said element contains at least one frequency different from the frequency of any incident beam of radiation, said different frequency being an even multiple of the frequency of one incident beam of electromagnetic radiation. In accordance with this invention, the optical element is formed from a poled organic glass composition (e.g., a film) of this invention.

Preferably, the emerging radiation of a different frequency is doubled (second order) (SHG). Preferably, the electromagnetic radiation is radiation from one of a number of common lasers, such as Nd-YAG, Raman-shifted Nd-YAG, Nd-YLF or Nd-glass, semiconductor diode, Er-Glass, Ti-Sapphire, dye, and Ar or Kr ion, or radiation shifted to other frequencies by nonlinear processes. For example, polarized light of wavelength 1.06$\mu$ from an Nd-YAG laser is incident on the optical element along the optical path. A lens focuses the light into the optical element. Light emerging from the optical element is collimated by a similar lens and passed through a filter adapted to remove light of wavelength 1.06$\mu$ while passing light of wavelength 0.53$\mu$.

It will be further apparent to those skilled in the art that the optical elements formed of the poled organic glass compositions of the invention are useful in other devices utilizing their nonlinear properties, such as devices utilizing the electro-optic effect.

As disclosed in U.S. Pat. No. 4,909,964, one conventional type of electro-optic modulator comprises means to direct a coherent beam into an optical element, and means to apply an electric field to said element in a direction to modify the transmission property of said beam. In accordance with this invention, the optical element is formed from a poled organic glass composition (e.g., a film) of this invention.

For example, in an electro-optic modulator comprising an optical element, a pair of electrodes is attached to the upper and lower surfaces of the element, across which a modulating electric field is applied from a conventional voltage source. The optical element is placed between two polarizers. A light beam (such as that from a Nd-YAG laser) is polarized by a polarizer, focused on the optical element and propagated therethrough, and subjected to modulation by the electric field. The modulated light beam is led out through an analyzer polarizer. Linearly polarized light traversing the optical element is rendered elliptically polarized by action of the applied modulating voltage. The analyzer polarizer renders the polarization linear again. Application of the modulating voltage alters the birefringence of the optical element and consequently the ellipticity impressed on the beam. The analyzer polarizer then passes a greater or lesser fraction of the light beam as more or less of the elliptically polarized light projects onto its nonblocking polarization direction.

Practice of the invention will become further apparent from the following non-limiting Examples.

EXAMPLES

In the experimental Examples which follow several different procedures were used to form the poled monomeric glass film.

Film Forming Procedure 1

Solvent Casting

A concentrated solution of the monomeric glass forming composition was prepared at room temperature. The concentration of the solution was chosen in each to provide a film typically about 1 $\mu$m thick. A conventional spin coating device having a rotational speed of approximately 1000 rpm was utilized to coat this solution onto the conductive side of a glass slide coated with indium tin oxide. The solvent was then evaporated from the resulting film by drying at room temperature for 24 hours. To minimize the possibility of crystal formation in the film, the film was heated to a temperature above its melting point and quenched by moving the slide to a cool metal block.

Film Forming Procedure 2

Melt Quenching

In this procedure one piece of indium tin oxide coated glass and a piece of uncoated slide protected by a 1 mil Teflon ® TFE film were separated by a 3 mil Teflon ® TFE spacer which has a 1 cm diameter hole in it. Powdered monomeric glass forming compositon was put in the hole formed in the spacer. The entire assembly was heated to slightly above the melting point of the monomeric glass forming composition while the two pieces of glass were pressed together to contain the molten glass within the 3 mil thick hole. The assembly was then quickly cooled. The top piece of glass and the protective film were then removed.

Poling Procedure 1

Poling or orientation of the nonlinear molecules in the monomeric glass was accomplished using an apparatus which included an insulated heated sample holder which holds the sample at an angle of 45° with respect to a beam from a Q-switched Nd-YAG laser. A corona assembly comprised of a wire and shield was positioned in such a way that the corona wire was approximately 1 cm above the sample. Small holes were provided in the corona shield and in the sample holder and aligned to permit the input laser beam to pass through both the sample and apparatus and second harmonic light generated by the sample to pass out of the apparatus. The second harmonic was used to monitor the degree of molecular alignment during the poling process.

In practice, after the sample (i.e., the unoriented glassy film on indium tin oxide coated glass) was placed in the sample holder, the indium tin oxide conductive coating on the glass was connected to ground. A +7000 volt potential was then applied to the corona electrode creating a positive corona in the region between the electrode and the sample. Positive ions were carried to the sample surface increasing the potential drop across the sample until its acceptance potential was reached. In a typical sample the resultant internal field was approximately $10^6$ V/cm. With the field still present, the temperature was increased to the film's glass transition temperature, Tg. As the sample neared Tg the second harmonic signal increased. The sample was held at Tg until the second harmonic signal no longer increased, at which time the sample was cooled in the presence of the field to room temperature.

EFISH Measurement Procedure

The electric field induced second harmonic generation (EFISH) was measured in accordance with the procedure described in L.-T. Cheng et al., "Nonresonant EFISH and THG Studies of Nonlinear Optical Property and Molecular Structure Relations of Benzene, Stilbene, and other Arene Derivatives", SPIE Nonlinear Optical Properties of Organic Materials II, Vol. 1147 (1989) which is hereby incorporated herein by reference.

Glass Transition Measurement Procedure

The glass transition and other thermal transitions were measured by differential scanning calorimetry according to methods outlined in E. A. Turi, ed. "Thermal Characterization of Polymeric Materials", Academic Press, 1982, N.Y. and W. W. Wendlandt, "Thermal Methods of Analysis", 2nd Ed., John Wiley and Sons, 1982, New York. The glass transition temperature (Tg) was recorded as the midpoint of the step change in heat flow (heat capacity) during heating (typically at 20° C./min) of samples contained in small aluminum pans which had been cooled from above the melting point at 20° C./min or faster. In cases where the samples crystallized at some temperature above the Tg this exothermic, first order transition peak temperature is recorded as TC. The temperature spread between Tg and Tc defined the useful range for working with the compounds above Tg where the possibility of crystallization is small. On further heating of crystalline samples, melting is observed as an endothermic, first order process; the peak temperature of melting is recorded as Tm.

EXAMPLE I

N-p-Nitroanilinoglutarimide 3 g of p-nitrophenylhydrazine and 2 g of glutaric anhydride in 20 ml THF ("tetrahydrofuran") were stirred for 15 min at room temperature. Analysis by infrared spectroscopy showed high conversion to amide-acid. To the reaction mixture was added 2 g of acetic anhydride, 1 ml of triethylamine which as then heated to near reflux. 50 mg of colbalt(II) acetate was added which induced an exothermic reaction. Analysis (IR) after a few minutes showed high conversion to imide. The mixture was evaporated under nitrogen and then slurried with ethanol. The ethanol soluble fraction (main product) was removed and concentrated to 3.4 g of brown solid. This solid was washed twice with benzene to remove 0.2 g and then crystalized from methanol to yield yellow needles, mp=197–198° C. The structure was confirmed by elemental analysis, IR and NMR. DSC analysis showed no crystallization when the melt was cooled at 20° C./min. On reheating a Tg was detected at 65° C., a Tc was detected at 120° C. and a Tm was detected at 204° C. Thin films cast from THF were glassy (noncrystalline) with Tg of 65° C. and were shown, by IR, to contain hydrogen bonds involving the carbonyl and N-H groups. On heating to 120° C., crystallization occured and the H-bonding was lost. High viscosity above Tg was observed by the resistance to sliding of two glass plates sandwiching a thin film of the compound. The $\mu\beta$, determined by EFISH in dioxane, was $26 \times 10^{-48}$ esu. Thin films were prepared on a conducting glass by spin coating using Film Forming Procedure 1 and were poled using Poling Procedure 1. The resulting material retained a substantial portion of the induced molecular ordering for more than 6 months. The induced $d_{33}$ determined from SHG Measurements was $\simeq 4 \times 10^{-12}$ m/V.

EXAMPLE II

N-p-heptafluoropropylsulfonylanilinoglutarimide

A solution of 1 g of p-heptafluoropropylsulfonylfluorobenzene, 1.34 g of hydrazine sulfate and 0.95 g of potassium carbonate in 10 ml of DMSO was heated at 110° C. for 3 hours after which time it was cooled, filtered and added to 200 ml of water. Insoluble product was removed by filtration and dried at 90° C. under vacuum. 0.738 g of white solid with m.p.=137.4–140° C. (hot stage microscope) and NMR consistent with p-heptafluoropropylsulfonylphenylhydrazine was obtained.

A mixture of 0.4 g of the above product and 0.15 g of glutaric anhydride in 5 ml of THF was refluxed for 15 min to form the amide-acid. 0.15 g acetic anhydride, 0.07 ml of triethylamine and 10 mg of cobalt(II)acetate were then added and the mixture was refluxed for 20 min. The solvent was evaporated under nitrogen and the product purified by flash chromotography on alumina developed with ether. The main fraction was a white solid with a Tg of 45° C. and exhibited no tendency to crystallize from the melt. The structure was confirmed by NMR and IR. Thin films were prepared on a conducting glass by spin coating using Film Forming Procedure 1 and were poled using Poling Procedure 1. During poling, a large SHG signal was noted when the field was first applied which decreased to near zero with time. After poling, crystallization of the sample was noted, most likely accounting for the signal decrease. The presence of the initial SHG signal indicated molecular alignment of the glasses state.

EXAMPLE III

N-p-heptadecylfluorooctylsulfonylanilinoglutarimide

A solution of 4.7 g of heptadecylfluorooctylsulfonylfuorobenzene, 3.29 g of hydrazine sulfate and 3.5 g of potassium carbonate in 60 ml of DMSO was heated at 100° C. for 4 hours, then cooled and added to 600 ml of water. The insoluble product was collected by filtration and dried at 90° C. under vacuum. This product (4.4 g) was recrystallized from ethanol to yield 2.9 g of material with m.p. of 145° C. and NMR consistent with p-heptadecylfluorooctylsulfonylphenylhydrazine.

The reaction of Example I was repeated except that p-heptadecylflurooctylsulfonylphenylhydrazine was used rather than p-nitrophenylhydrazine. The product readily formed a glass when quenched from the melt with Tg of 54° C., Tc of 130° C. and Tm of 171° C. A transparent film was formed by heating a sample of the product above 171° C. between two glass slides and cooling to room temperature.

EXAMPLE IV 3,5-Dihydroxyacetophenone, p-nitrophenylhydrazone

A mixture of 0.25 g of 3,5-dihydroxyacetophenone, 0.25 g of p-nitrophenylhydrazine and 5 drops of acetic acid in 10 ml of ethanol was refluxed for 1 hr and then stirred at room temperature for 16 hr. An orange solid separated when the mixture was poured into water, and the solid was recrystallized from ethanol/water to yield 0.36 g of orange crystals, m.p.=235–240° C. The structure was confirmed by NMR, IR and elemental analysis. The material formed a glass when cooled from the melt with Tg of 123° C. and showed no tendency to crystallize from the melt. Glassy films were cast from THF and pyridine. The $\beta$ (EFISH) was determined to be $5 \times 10^{-30}$ esu. Films were prepared by spin coating from THF using Film Forming Procedure 1 and were poled using Poling Procedure 1. During poling, a large SHG was noted when the field was first applied which decreased to near zero with time. The presence of the initial SHG signal indicates molecular alignment of the glassy state. Crystallization was noted and may have caused the signal to decay with time.

EXAMPLE V

N-(p-Cyanophenyl)aminomethylsuccinimide

N-(p-Cyanophenyl)aminomethylsuccinimide was prepared by the method described in S. B. Kadin Monomethylation of Aromatic Amines via Sodium Borohydride Mediated Carbon-Nitrogen Bond Cleavage, J. Org. Chem 38 (7) 1973 pp. 1348–1350 and was shown to readily form a glass on rapid cooling from the melt with Tg of 43° C., Tc of 99° C. and Tm of 194° C. A sample for poling was prepared using Film Forming Procedure 2 and was poled using Poling Procedure 1. The sample maintained at least one-third of its initial alignment for a period of approximately two weeks before large sections of the sample spontaneously crystallized.

EXAMPLE VI

N-(p-Carboxymethylphenyl)aminomethylsuccinimide

N-(p-Carboxymethylphenyl)aminomethylsuccinimide was prepared by the method described in S. B. Kadin J. Org. Chem. 38 (7), supra. 15.11 g of methy-4-amino-benzoate, 11.9 g of succinimide and 9.1 ml of 37% aqueous formaldehyde in 120 ml of ethanol were reacted under reflux for 2 hrs. 18.7 g of white solid, filtered from the mixture had a Tm of 200–203° C. and an NMR consistent with the desired product. On rapid cooling from the melt a glass was formed with Tg of 39° C., Tc of 92° C. and Tm of 203° C. A sample was prepared using Film Forming Procedure 2 and was poled using Poling Procedure 1. Short term stability was achieved, but a total loss of signal was observed after three days, most likely the result of crystallization to a centrosymmetric structure.

EXAMPLE VII

N-(4'-nitro-4-stilbenvl)aminomethylsuccinimide

N-(4'-nitro-4-stilbenyl)aminomethylsuccinimide, a deep red solid, was prepared by the method described in S. B. Kadin J. Org. Chem. 38 (7), supra, using 0.32 g of '-nitro-4-amino stilbene, 0.15 g of succinimide and 0.15 ml of 37% formaldehyde. The product readily formed a glass when cooled from the melt, with Tg of 71° C., Tc of 131° C. and Tm's of 210° C. and 235° C. Thin glassy films were cast from 1,1,2,2-tetrachloroethane. A sample was prepared using Film Forming Procedure 2 and was poled using Poling Procedure 1. A SHG signal was observed during poling. Short term stability was achieved. However, the SHG signal decayed by more than a factor of three during the first hour with no poling field. Measurements made several days later showed crystallization and much higher SHG signal, most likely the result of crystallization into an acentric structure.

EXAMPLE VII (p-Nitrophenylvinylene)julolidine (p-Nitrophenylvinylene)julolidine was prepared by the addition of 9.37 g of julolidine carboxaldehyde to 9.06 g of 4-nitrophenyl acetic acid and 3.82 g of pyridine at 50° C., followed by heating at 125° C. for 115 min. The product, recrystallized from isopropanol, had a Tm of 164-165° C., and the structure was confirmed by NMR. The material had $\mu\beta$ above $800\times10^{-48}$ esu (EFISH) and readily formed a glass when cooled from the melt with Tg of 33° C., Tc of 78, and Tm's of 154 and 172. A sample was prepared using Film Forming Procedure 2 and was poled using Poling Procedure 1. A large signal was noted when the field was first applied, and then decreased to near zero with time. The presence of the initial SHG signal indicated molecular alignment of the glassy state. Some evidence of crystallization was noted after the poling was completed.

EXAMPLE IX 2-(4-Dimethylaminophenyl)-3,5,6-tricyanopyrazine 2-(4-Dimethylaminophenyl)-3,5,6-tricyanopyrazine was prepared using the method described in U.S. Pat. No. 3,963,715. The product readily formed a glass on rapid cooling from the melt with Tg of 60° C., a Tc of 75-135 and a Tm of 205° C. A transparent film was formed by heating above 205° C. between two glass slides and cooling to room temperature.

Films were prepared for poling by spin coating from DMF (dimethylformamide) using Film Forming Procedure 1 except that in this case the substrate was heated to 70° C. during the spin coating. The films were poled using Poling Procedure 1. The SHG signal induced during poling decayed rapidly after removal of the electric field, most likely due to the presence of unevaporated solvent.

EXAMPLE X p-Nitroanilinoglutamic acid

The intermediate amide/acid from Example I was recrystallized from ethanol to yield a crystalline solid, having a Tm of 142° C., which both upon cooling from the melt and upon casting from solution (THF) formed a stable glass film having a Tg of 31° C.

EXAMPLE XI

S-2(1-hydroxy-2.2-difluoroethylbenzene)-4-sulfonyl-4-aminobiohenyl p-Br-phenyl-SCF$_2$H was prepared using the general procedure of U.S. Pat. No. 4,837,327. DMAC. ("dimethyl acetamide") was used as co-solvent rather than p-dioxane. To 6 ml of water, 5.00 g of NaOH was dissolved and added to 6 ml of DMAC. containing 5.11 g (0.027 moles) p-bromothiophenol in a Fischer Porter bottle. The bottle was heated to 70° C. and pressurized to 50 psi of CF$_2$HCl. The bottle was periodically charged to 50 psi with CF$_2$HCl and kept at 70° C. for three hours. After cooling to room temperature, 50 ml of water and 100 ml of ether were added. The mixture was extracted with an additional 2×100 ml of ether. The extracts were washed with water and dried over MgSO$_4$. Some of the ether was removed by rotary evaporation and the residue distilled at 10 mm. 3.83 g (0.016 mmoles, 59%) of a colorless liquid was collected at 103° C. $^1$H nmr (CD$_2$Cl$_2$): 7.56 (m, 2H), 7.5 (m, 2H), 6.8 (t, J=56.6Hz, 1H). $^{19}$F nmr (CD$_2$Cl$_2$, F11): −91.5 (d, J=56.6 Hz, 2F).

p-Br-phenyl-SO$_2$CF$_2$H was prepared by dropwise adding 15.81 g (55%, 0.052 moles) of MCPBA ("3-chloroperoxybenzoic acid") in 125 ml of CH$_2$Cl$_2$ to 4.82 g (0.0202 moles) of Br-phenyl-SCF$_2$H in 25 ml of CH$_2$Cl$_2$. The mixture was stirred at room temperature overnight and then refluxed for 3.5 hrs. The mixture was filtered and the solid washed with CH$_2$Cl$_2$. The organic layer was added to saturated NaHCO$_3$ (100 ml). The organic layer was washed with 100 ml of water and then dried over MgSO$_4$. The solvent was removed and the residue chromatographed on silica gel eluted with CHCl$_3$; thus obtained was 4.788 g (0.0177 moles, 87%) of the desired product as a white solid. $^1$H nmr (CD$_2$Cl$_2$): 7.8 (s, 4H), 6.2 (t, J=53.3 Hz, 1H). $^{19}$F nmr (CD$_2$Cl$_2$): −122.0 (d, J=53.3 Hz).

Following the general procedure of U.S. Pat. No. 4,837,327, 0.363 g (3.42 mmoles) of benzaldehyde was added to 0.300 g (1.11 mmoles) of p-Br-phenyl-SO$_2$CF$_2$H in 3 ml of CH$_2$Cl$_2$ and 3 ml of 50% NaOH in water, and a drop of Aliquat 336® was added as a phase transfer catalyst. The mixture was stirred for about 4 hrs. 50 ml of 1 N HCl was added to this mixture and the acidified mixture was extracted twice using 30 ml of CH$_2$Cl$_2$. The organic layer was dried over MgSO$_4$, the solvent was removed and the residue was chromatographed on silica gel eluted initially with 50% CH$_2$Cl$_2$/hexane. The product was eluted with ethyl acetate to give 0.271 g of the crude product as a yellow oil. This was washed with hexane to induce crystallization to a white solid (0.202 g, 0.53 mmoles, 48%). 1H nmr (CD$_2$Cl$_2$): 7.8 (m, 4H), 7.4 (m, 5H), 5.6 (d of t, 1H), 3.1 (d, 1H) (i.e., Br-phenyl-SO$_2$CF$_2$C(Ph)(H)-(OH).

1.00g (2.65 mmoles) of Br-phenyl-SO$_2$CF$_2$C(Ph)(H)(OH) and 50 mg of Pd(PPh$_3$)$_4$ were stirred for 10 minutes in about 7 ml of dioxane. To this mixture was added 1.737 g (5.30 mmoles) of Me$_3$SnSn-Me$_3$ in 2 ml of dioxane. The mixture was refluxed overnight. Solvent was removed by rotary evaporation and the residue was chromatographed over silica gel eluted with 25% EtOAc/hexane to give 1.207 g (2.6 mmoles, 99%) of the desired product as a white solid. Elemental analysis calculated for C$_{17}$H$_{20}$O$_3$F$_2$SSn: C: 44.28; H: 4.37; found: C: 44.44; H: 4.63. $^1$H nmr (CD$_2$Cl$_2$): 8.9 (d, 2H), 8.8 (d, 2H), 7.5 (m, 2H), 7.5 (m, 2H), 5.5 (d of t, 1H), 3.3 (d, 1H), 0.4 (s with Sn Satellite, 9H). $^{19}$F nmr (CD$_2$Cl$_2$, F11):−104.45 (dd, J=237.7, 2.9 Hz, IF), −119.21 (dd, J =237.7, 20.9 Hz, 1F) (i.e., Me$_3$Sn-phenyl-SO$_2$CF$_2$C(Ph)(H)(OH)).

0.172 g (0.67 mmoles) of (CH$_3$C(O))$_2$N-phenyl-Br and 25 mg of Pd(PPh$_3$)$_4$ were stirred for 10 minutes in about 2 ml of dioxane. To this mixture was added 0.309 g (0 67 mmoles) of Me$_3$Sn-phenyl-SO$_2$CF$_2$C(Ph)(OH)(H) in 1 ml of dioxane. The mixture was refluxed overnight. Solvent was removed and the residue chromatographed with 25% EtOAc/hexane to give 0.164 g (0.35 mmoles, 52%) of the desired product as a colorless liquid. Elemental analysis calculated for $C_{24}H_{21}NO_5F_2S$: C: 60.88; H: 4.47; found: C: 60.03, 59.67; H: 4.66, 4.75. $^1H$ nmr ($CD_2Cl_2$) 8.1 (d, 2H), 7.9 (d, 2H), 7.7 (d, 2H), 7.5 (m, 2H), 7.4 (m, 3H), 7.3 (d, 2H), 5.6 (d of t, 1H), 3.3 (d, 1H), 2.3 (s, 6H). $^{19}F$ nmr ($CD_2Cl_2$, F11): −104.29 (dd, J=238, 3, 1F), −118.72 (dd, J=238, 22, 1F).

1.550 g (3.27 mmoles) of $(CH_3C(O))_2$N-biphenyl-$SO_2$-$CF_2C(Ph)(H)(OH)$ produced as above was dissolved in 10 ml of EtOH and 10 ml of concentrated HCl was added. The mixture was refluxed overnight. The mixture was cooled to room temperature and 40 ml of 2N NaOH, 80 ml of $CH_2Cl_2$ and 40 ml of water were added. The aqueous layer was extracted twice more with 80 ml of $CH_2Cl_2$. The aqueous layer was then neutralized with 2N HCl to pH around 6–7 and extracted once more with 80 ml of $CH_2Cl_2$. The organic layer was dried over $Na_2SO_4$, filtered, and solvent removed to give 1.030 g (2.65 mmoles, 81%) of $H_2$N-biphenyl-$SO_2CF_2C(Ph)(OH)(H)$ or S-2(1-hydroxy-2,2-difluoroethylbenzene)-4-sulfonyl-4′aminophenyl). $^1H$ nmr ($CD_2Cl_2$): 8.0 (m,2H), 7.8 (m,2H), 7.55 (m,4H), 7.45 (m, 3H), 6.8 (m, 2H), 5.6 (d of t, J=21.1, 3.6 Hz, 1H), 4.0 (s, 2H), 3.3 (d, J=4.1Hz,1H). $^{19}F$ nmr ($CD_2Cl_2$): −104.6 (d, J=237.7Hz, 1F), −119.5 (dd, J=237.7, 20.9 Hz, 1F). Elemental analyses calculated for $C_{20}H_{17}SO_3NF_2$: C: 61.69; H: 4.40; Found: C: 61.52; H: 4.40.HRMS: measured: 389.0849 m/e; calculated: 389.0897 for $C_{20}H_{17}NO_3F_2S$. This compound melted at 169° C. and formed a glass (Tg=54° C.) when cooled rapidly from the melt and remained noncrystalline up to 110° C. on heating above the Tg at 20° C./min. Clear, colorless glassy films were readily cast from solutions of the compound in THF.

Films were prepared for poling by spin coating from DMF (dimethylforamide) using Film Forming Procedure 1 except that in this case the substrate was heated to 70° C. during the spin coating. The films were poled using Poling Procedure 1. The SHG signal induced during poling decayed rapidly after removal of the electric field most likely due to the presence of unevaporated solvent.

EXAMPLE XII 3.5-Dihvdroxyacetophenone, p-heptafluoropropyl-sulfonylphenylhydrazone 0.5 g of p-heptafluoropropylsulfonylphenylhydrazine, 1.24 g of 3,5-dihydroxyacetophenone and 5 drops of acetic acid in 20 ml of ethanol were heated at 80° C. for 5 hours, cooled to room temperature and added to water. The insoluble product was filtered from the solution, washed and dried to yield 0.6 g of yellow solid. Recrystallization from ethanol gave crystals with Tm=232° C. A sample heated above 232° C. between 2 glass slides and then cooled to room temperature formed a transparent, thin, hard glassy film. A Tg was measured as 87° C., and a Tc was measured as 139° C.

EXAMPLE XIII 3.5-Dihydroxyacetophenone, p-heptadecylfluorooctylsulfonylphenylhydrazone 0.5 g of p-heptadecylfluorooctylsulfonylphenylhydrazine, 2.31 g of 3,5-dihydroxyacetophenone and 5 drops of acetic acid in 20 ml of ethanol were heated at 80° C. for 4 hours, cooled to room temperature and added to 200 ml of water. Insoluble product was filtered from solution, washed and dried to yield 0.307 g of yellow solid. This product had a Tg of 84° C., a Tc of 199° C. and a Tm of 228° C. A sample heated above 230° C. between 2 glass slides and then cooled to room temperature formed a transparent, thin glassy film.

EXAMPLE XIV

S-2(1-hydroxy-2,2-difluoroethylbenzene)-4-sulfonyl-4′-N-acetylaminoohenyl)

105 mg (0.22 mmoles) of $(CH_3C(O))_b$ $_2$N-biphenyl-$SO_2CF_2C(Ph)(H)(OH)$ was dissoved in 1 ml of EtOH and 1 ml of concentrated HCl was added. The mixture was stirred overnight. To the white slurry was added 2N NaOH to pH of 14 and saturated $NH_{40}OH$ was added to adjust the pH to 9. The mixture was filtered and washed with water to give 85 mg (0.22 mmoles, 100%) of $(CH_3C(O))(H)$N-biphenyl-$SO_2CF_2C(Ph)(OH)(H)$ or S-2(1-hydroxy-2,2-difluoroethylbenzene)-4-sulfonyl-4′-N-acetylaminophenyl). $^{19}F$ nmr ($CD_2Cl_2$, F11): −103.4 (dd, J=237, 5 Hz, 1F), −116.1 (dd, J=237, 21.5 Hz, 1F). In a separate experiment, a slurry of the bisacetyl (0.710 g, 1.50 mmoles) in 30 ml of EtOH was added to 30 ml of concentrated HCl. The mixture was stirred overnight and then filtered, washed with water. The solid was added to 10–15 ml of water and the pH adjusted to 7 with 1N NaOH. The solid was filtered and washed with water to give 0.526 g (1.22 nmoles, 81%) of $(CH_3C(O))(H)$N-biphenyl-$SO_2CF_2C(Ph)(OH)(H)$. $^1H$ nmr (DMSO-$d_6$): 10.2 (s, 1H), 8.0 (s, 4H), 7.8 (s,4H), 7.45 (m, 2H), 7.38 (m, 3H), 6.9 (broad d, 1H), 5.4 (d of m, 1H), 3.4 (s, 3H). IR(KBr): 1670 cm$^{-1}$. HRMS: measured: 431.1037; calculated: 431.1003 for $C_{22}H_{19}NO_4F_2S$. This compound melted at 261° C., formed a glass (Tg=75° C.) when cooled slowly from the melt, and remained noncrystalline up to 150° C. when heated above the Tg at 20° C./min. Clear, colorless glassy films were readily cast from solutions of the compound in DMF (i.e., "dimethyl formamide"), DMSO (i.e., "dimethyl sulfoxide"), THF and THF/DMF mixtures.

EXAMPLE XV $(CH_3)(CH_3C(O))$N-biphenyl-$SO_2CF_2C(Ph)(H)(OH)$ 0.247 g (1.08 mmoles) of $(CH_3)(CH_3 C(O))$N-phenyl-Br and 20 mg of $Pd(PPh_3)_4$ were stirred for 10 minutes in about 1 ml of dioxane. To this mixture was added 0.500 g (1.08 mmoles) of $Me_3Sn$-phenyl-$SO_2CF_2C(Ph)(OH)(H)$ in 3 ml of dioxane. The mixture was refluxed for 5 days. Solvent was removed and the residue chromatographed with 50% EtOAc/hexane to give 0.313 g (0.70 mmoles, 65%) of the desired product as a white solid. $^1H$ nmr ($CD_2Cl_2$): 8.1 (m, 2H), 7.9 (m, 2H), 7.75 (m, 2H), 7.5 (m, 2H), 7.43 (m, 3H), 7.39 (m, 2H), 5.6 (d of t,J=21 , 3.4 Hz, 1H), 3.42 (d, J=4 Hz, 1H), 3.3 (s, 3H), 1.97 (s, 3H). $^{19}F$ nmr (DMSO-$d_6$, F11): −103.25 (dd, J=237, 4.2, 1F), −115.99 (dd, J=237, 21.6, 1F). This compound was partially glassy as prepared with a crystalline component melting around 200° C. It formed a glass (Tg=50° C.) on cooling from the melt and remained noncrystalline up to 90° C. on heating above Tg at 20° C./min. Clear, colorless glassy films were readily prepared by casting from a solution of the compound in THF.

EXAMPLE XVI $(CH_3)(H)$N-biphenyl-$SO_2CF_2C(Ph)(H)(OH)$

To 0.254 g (0.57 mmoles) of the compound prepared above was added 1 ml of EtOH and 1 ml of concentrated HCl and the mixture was refluxed overnight. To the cooled mixtured was added 10 ml of 2N NaOH and 10 ml of $CH_2Cl_2$. The aqueous layer was extracted once more with 10 ml of $CH_2Cl_2$. The pH of the aqueous layer was adjusted to 7 with 2N HCl and extracted once more with 10 ml of $CH_2Cl_2$. The combined organic layer was dried over $Na_2SO_4$ and the solvent removed to give 0.178 g (0.43 mmoles, 75%) of the desired product. $^1H$ nmr ($CD_2Cl_2$): 8.0 (m,2H), 7.8 (m, 2H), 7.58 (m, 2H), 7.5 (m, 2H), 7.4 (m, 3H), 6.7 (m, 2H), 5.6 (d of t, J=21, 3.4 Hz, 1H), 4.1 (s, 1H), 3.39 (d, J=4 Hz, 1H), 2.88 (s, 3H). This compound was partly glassy as prepared with a crystalline component melting at 123° C. It formed a glass (Tg=42° C.) on cooling from the melt and remained noncrystalline up to 150° C. on heating above the Tg at 20° C./min.

Particular embodiments of the invention are included in the Examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A poled organic glass composition which consists essentially of the compound N-p-nitroanilinoglutarimide.

2. A poled composition in accordance with claim 1 in the shape of a film.

3. A compound which is N-p-nitroanilinoglutarimide.

* * * * *